United States Patent [19]
Lavia

[11] Patent Number: 5,068,886
[45] Date of Patent: Nov. 26, 1991

[54] CATHETER OR CANNULA POSITION INDICATOR FOR USE IN HEMODYNAMIC MONITORING AND THE LIKE

[76] Inventor: Monica Lavia, 3524 Hickory, Omaha, Nebr. 68105

[21] Appl. No.: 544,968

[22] Filed: Jun. 28, 1990

[51] Int. Cl.$^5$ .............................................. H05G 1/28
[52] U.S. Cl. ..................................... 378/164; 378/210
[58] Field of Search ................................. 378/163, 164

[56] References Cited

U.S. PATENT DOCUMENTS

| | | | |
|---|---|---|---|
| 3,590,818 | 7/1971 | Lemole | 128/214 |
| 3,687,142 | 8/1972 | Leibinzohn | 128/348 |
| 3,812,842 | 5/1974 | Rodriquez | 128/2 A |
| 3,847,157 | 11/1974 | Caillouette et al. | 128/348 |
| 3,996,927 | 12/1976 | Frank | 128/2.05 D |
| 4,160,448 | 7/1979 | Jackson | 128/673 |
| 4,279,252 | 7/1981 | Martin | 128/349 |
| 4,469,483 | 9/1984 | Becker et al. | 604/280 |
| 4,489,454 | 12/1984 | Thompson | 5/503 |
| 4,546,774 | 10/1985 | Haught | 128/683 |
| 4,669,484 | 6/1987 | Masters | 128/673 |
| 4,918,715 | 4/1990 | Krupnick et al. | 378/164 |

OTHER PUBLICATIONS

Urban, N., *Integrating Hemodynamic Parameters with Clinical Decision-Making*, 6 Critical Care Nurse 48.
Kirchhoff, K. et al., *Mean Arterial Pressure Readings: Variations with Positions and Transducer Level*, 33 Nursing Research 343 (Nov./Dec.1984).
Schermer, L., *Physiologic and Technical Variables Affecting Hemodynamic Measurements*, 8 Critical Care Nurse 33.
Lough, M., *Introduction to Hemodynamic Monitoring*, 22 Nursing Clinics of North America 89 (Mar. 1987)

*Primary Examiner*—Craig E. Church
*Attorney, Agent, or Firm*—John A. Beehner

[57] ABSTRACT

A catheter position indicator for use with leveling devices adapted for use in hemodynamic monitoring. The indicator includes a radio transparent sheet material containing a plurality of spaced apart radio opaque material portions. Also included is a means for fastening the sheet material to a human body. An X-ray may be taken so that the location of a catheter may be determined in relation to the radio opaque portions of the radio transparent sheet material. Once the location of the catheter is determined a simple bubble level device may be utilized to bring a hemodynamic transducer assembly into level with the inserted catheter.

11 Claims, 3 Drawing Sheets

CATHETER OR CANNULA POSITION INDICATOR FOR USE IN HEMODYNAMIC MONITORING AND THE LIKE

BACKGROUND O THE INVENTION

The present invention is directed generally to a method and apparatus for locating a catheter and more particularly to a method and apparatus for locating the position of a catheter so that a transducer assembly may be brought into the same horizontal plane as the catheter.

Physiological fluid pressure data is helpful in assessing the health of individuals. For example, intracranial pressure, intrauterine pressure, left atrial pressure, pulmonary artery pressure, and central venous pressure assist health care providers in prescribing and providing health care.

One indicator of a patient's health is her or his blood pressure. Blood pressure may be measured using both noninvasive and invasive techniques. The most common noninvasive techniques are palpation, ultrasound, and flush (each of which utilizes at least one sphygmomanometer cuff). Invasive or direct pressure measurement techniques are also available and widely used by health care providers.

Invasive or direct pressure techniques provide many advantages over noninvasive techniques. For example, long-term continuous observation permits monitoring slight trend-setting changes in the cardiovascular system; the effectiveness of fluid and medication therapies may be determined; and an accurate appraisal may be obtained even if a patient is in shock.

Hemodynamic monitoring of hospital patients requires that the zero (air) port of the monitoring transducer assembly be at the same level as the catheter.

Accordingly, a primary object of the present invention is to provide an improved method and apparatus for locating the position of a catheter.

Another object of the present invention is to provide a method and apparatus for locating the position of a catheter with a single x-ray.

Another object of the present invention is to provide a method and apparatus for locating the position of a catheter that is inexpensive, durable, easy to use, and safe.

Another object of the present invention is to provide a method and apparatus for locating the position of a catheter that is adapted for use with existing hemodynamic monitoring equipment.

Another object of the present invention is to provide a method and apparatus for locating the position of a catheter that allows a patient to be maintained, or repeatedly moved, as comfort requires, in any position necessary before and during hemodynamic monitoring.

Another object of the present invention is to provide a method and apparatus for locating the position of a catheter that does not increase patient trauma.

SUMMARY OF THE INVENTION

The present invention teaches a novel method and apparatus for locating the position of a catheter. The apparatus may be utilized with a leveling device for patient hemodynamic monitoring. The indicator includes a radio transparent sheet material containing a plurality of spaced apart radio opaque material portions. Also provided is a means for fastening the sheet material to a human body.

An X-ray may be taken so that the location of a catheter may be determined in relation to the radio opaque portions of the radio transparent sheet material. Once the location of the catheter is determined a simple bubble level device may be utilized to bring a hemodynamic transducer assembly into level with the inserted catheter

DESCRIPTION OF THE PREFERRED EMBODIMENT

Figure 1:
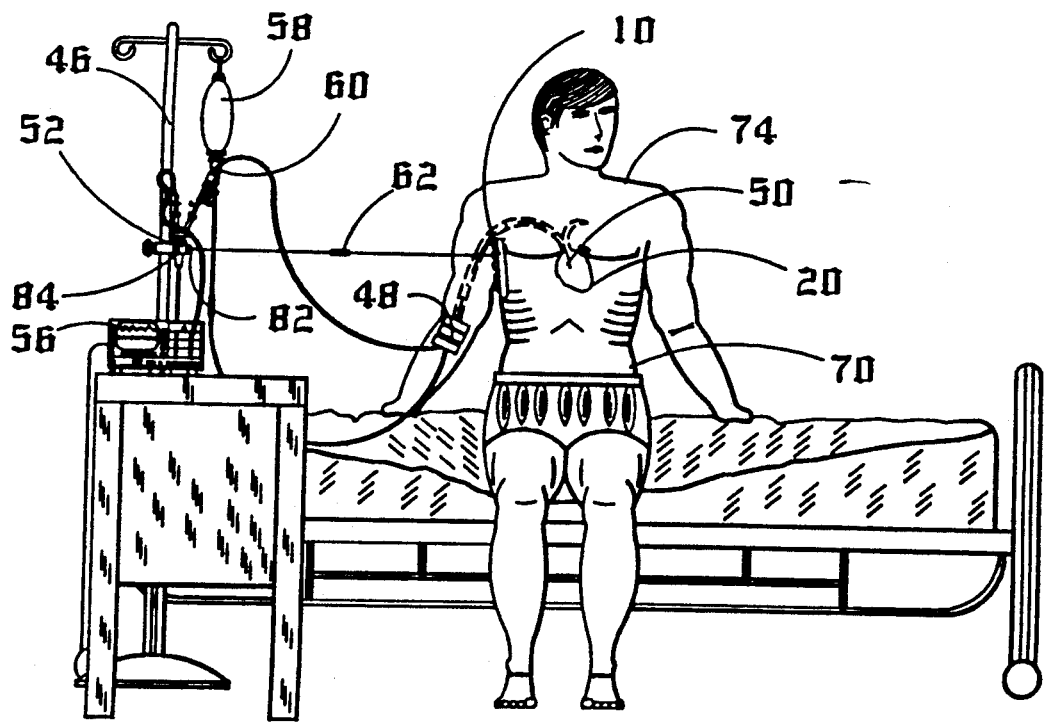
FIG. 1 is an elevational view illustrating a patient seated on a bed next to a nightstand with a pressure transducer assembly connected to an IV stand. Attached to the patient is the catheter position indicator. Also illustrated is a bubble level connected between the catheter position indicator apparatus and the zero level of the pressure transducer assembly.
Figure 2:
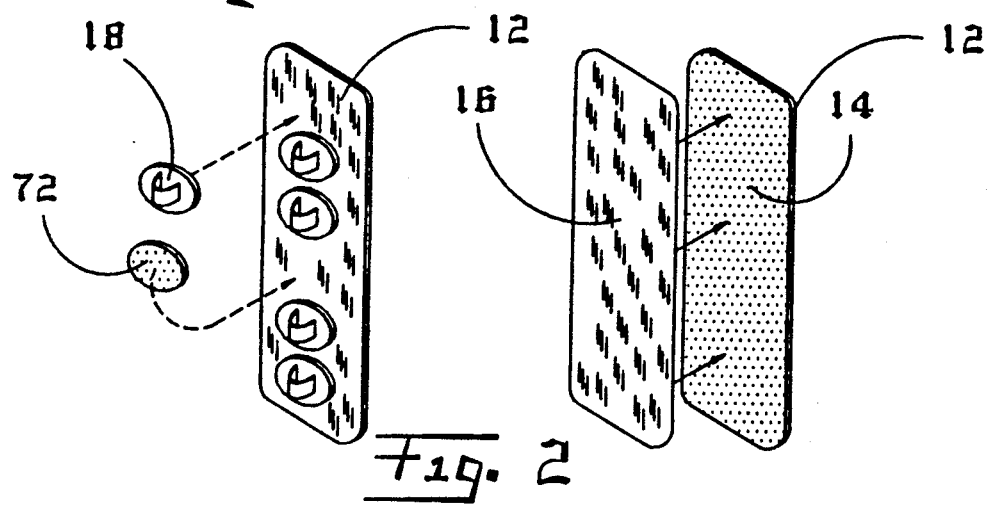
FIG. 2 is a perspective view of a preferred embodiment of the catheter position indicator showing the radio transparent sheet material, peel away adhesive protective back, and the radio opaque level engagement rings.
Figure 3:
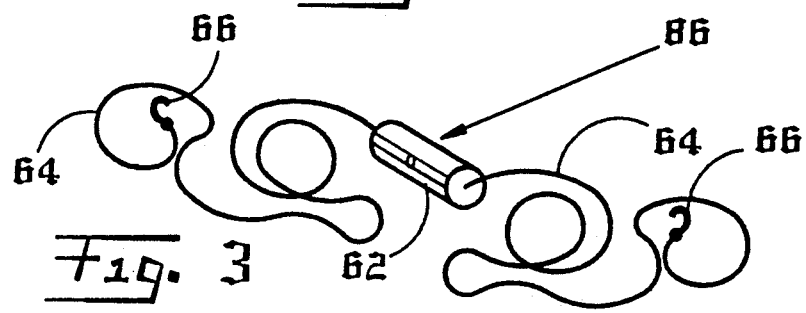
FIG. 3 is a perspective view of a string having hooked ends with a bubble level indicator supported thereon for connection between the catheter position indicator and the pressure transducer assembly.
Figure 4:
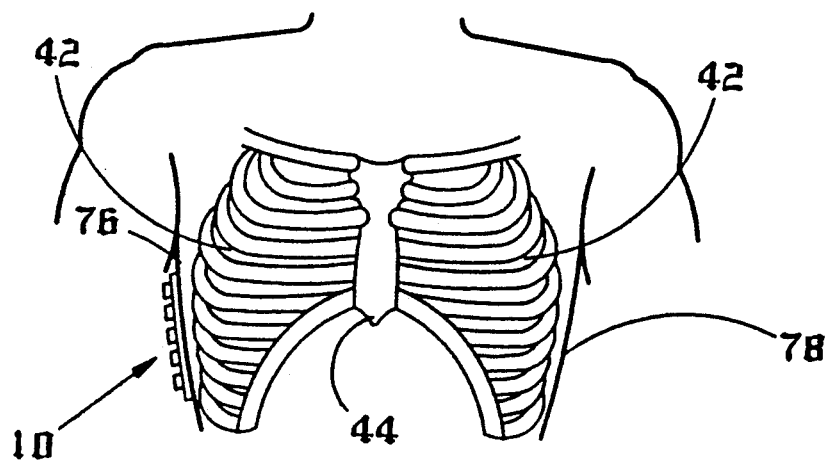
FIG. 4 is a partial front view of a patient showing the thoracic cavity in relation to the catheter position indicator.
Figure 5:
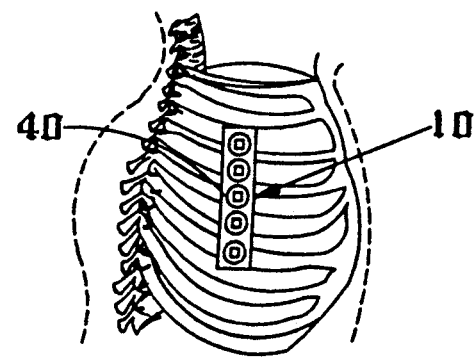
FIG. 5 is a side view of a patient showing the thoracic cavity in relation to the catheter position indicator.
Figure 6:
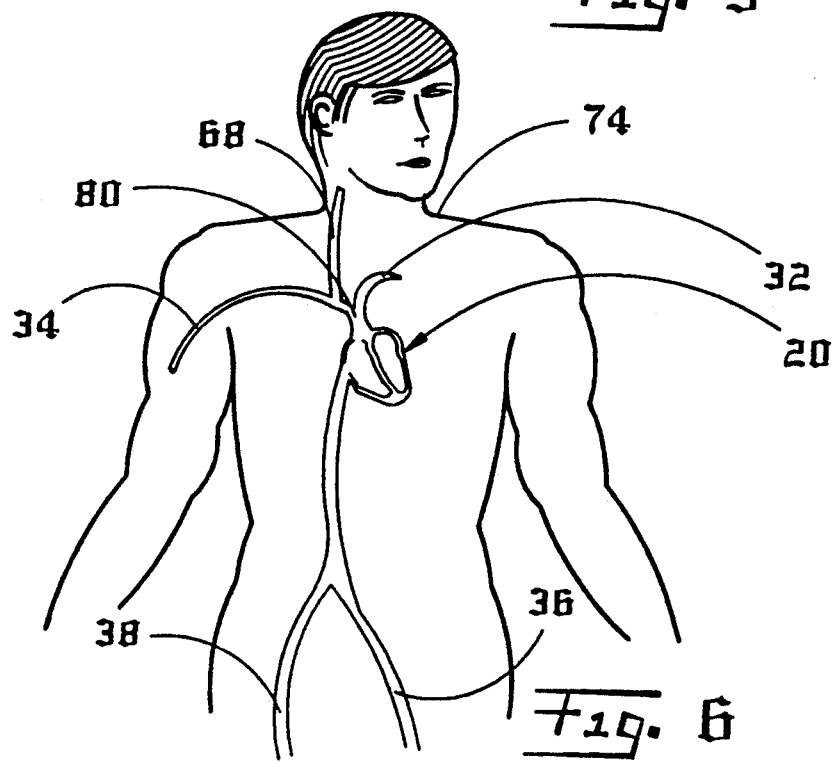
FIG. 6 is a partial front view of a patient with the catheter position indicator in place and showing alternative entry locations for the catheter.
Figure 7:
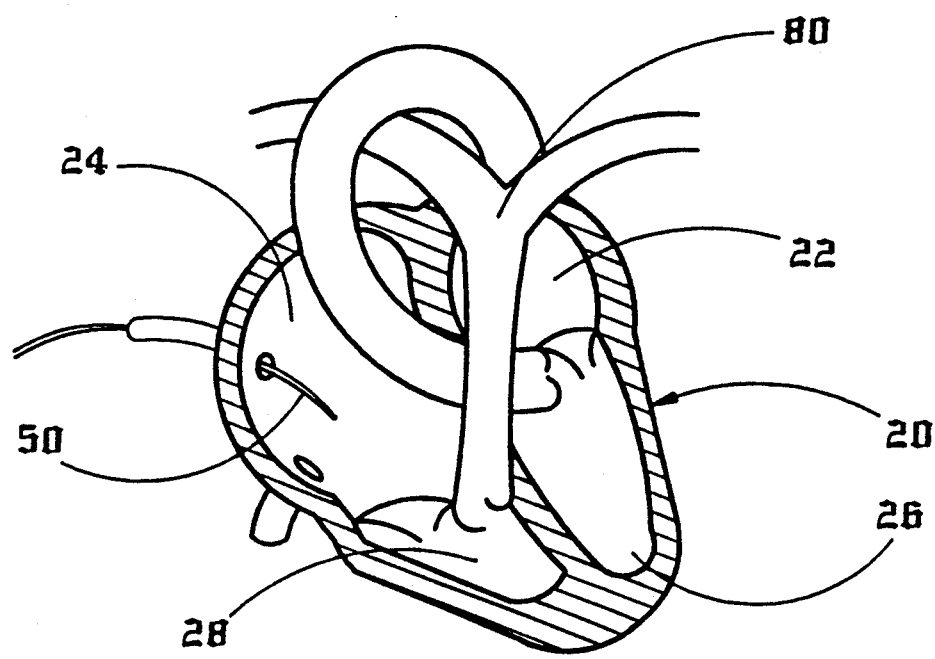
FIG. 7 is a partial enlarged, partial sectional detailed view showing the position of a catheter tip within the heart of a patient.
Figure 8:
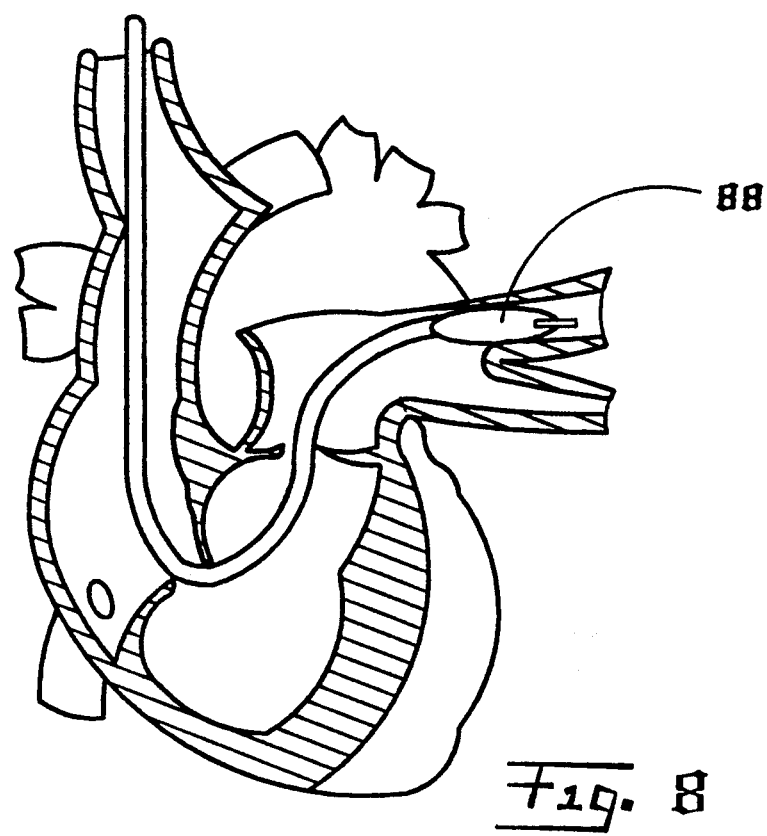
FIG. 8 is a partial enlarged, partial sectional detailed view showing the position of a Swan-Ganz catheter tip within the heart of a patient.

The catheter position indicator 10 is illustrated in FIG. 2. FIGS. 4 and 5 best illustrate the patient attachment location of the catheter position indicator 10. FIGS. 7 and 8 illustrate the human heart and the preferred position of two different types of catheters used for hemodynamic monitoring. FIG. 6 illustrates the preferred catheter insertion pathways for hemodynamic monitoring. FIG. 3 illustrates a common leveling device for attachment between the catheter position indicator and a pressure transducer assembly. FIG. 1 illustrates the catheter position indicator in use with a hemodynamic monitoring and leveling assembly.

The catheter position indicator 10 is preferably formed of a radio transparent sheet material 12 having an adhesive backing 14 for adhering the sheet material 12 to the epidermal layer 70 of the human body.

The adhesive backing 14 is preferably formed of a non-toxic tack adhesive capable of painless removal from the epidermal layer 70. Also included is a peel-away backing 16 for preventing the adhesive baokinq 14 from adhering to objects prior to placement of the catheter position indicator 10.

Affixed to the front surface of the radio transparent sheet material 12 are a plurality of spaced apart radio opaque hook fasteners 18. The fasteners 18 are spaced apart in a graduated fashion along the surface of the sheet material 12, and are adhered to the sheet material 12 by an adhesive 72.

Radio transparent materials are well known to the art. The sheet material 12 may be formed from an extrudable polyvinyly chloride with a high plasticizer content. One side of the radio transparent sheet material 12 may be calendar coated with a tack adhesive backing 14. So that the release paper or peel-away backing 16 does not become permanently adhered to the adhesive 14 it may be coated with silicon or any other suitable non-stick substance.

Radio opaque materials are well known to the art. The fasteners 18 may be formed of a length of cord treated with a radio opaque dye, stainless steel, or other metallic substance. However, in a preferred embodiment the fasteners as may be formed of a polymer such as nylon or polyvinylchloride with a high metallic powder content.

Additionally, although not shown in the drawings, a rule may be formed within the radio transparent sheet material 12 that has radio opaque graduations along its surface. In this fashion a single fastener 18 may be removably adhered by a hook and loop type fastener along the surface of the catheter position indicator 10.

In operation the catheter position indicator 10 may be utilized as follows. A patient 74, in either a supine, semi Fowler, or seated position may have her or his arm raised so as to expose the axillary region 76. The area may be shaved so as to permit the adhesive 14 of the indicator 50 from adhering to any hair that might be present. The peel-away backing 56 may be removed from the indicator 10 and the indicator, adhesive side first, may be adhered against the epidermal layer 70 of the patient 74.

The indicator 50 should be placed so that it is centered around the phlebostatic axis 40 of the patient 74 (FIGS. 4 and 5). The phlebostatic axis 40 is located at the intersection of the fourth intercostal space 42 where it joins the sternum 44 and the mid axillary line. In this way the indicator 50 covers the outermost point of the posterior chest 72 (FIGS. 4 and 5).

Several physiological fluid pressures are important health indicators in clinical medicine. For example, where peripheral arterial pressure data is necessary a catheter 50 may be inserted through the radial, brachial hz, axillary, or femoral 36 arteries.

Additionally, a determination of mean arterial pressure is helpful in indicating the functional pressure that exists in the peripheral arterial system during all phases of the cardiac cycle. Mean arterial pressure may be measured with a catheter do inserted through the radial, brachial 32, axillary, Or femoral 36 arteries.

Further, where efficient regulation of fluid replacement is necessary, central venous pressure may be utilized as a guide. The catheter 50 may be inserted into the left or right brachial vein 34 and passed into the superior vena cava 8.

Where left ventricular 26 performance data is necessary the catheter 10 may be passed far enough into the pulmonary artery 30 so that left atrium 22 pressure is measured (left atrium pressure is considered a good indicator of left ventricle filling pressure). In this procedure the catheter 50 is usually introduced through a large vein in the antecubital area.

Moreover, during a thoracotomy it is useful to measure left arterial pressure. This is usually accomplished by placing a catheter 50 directly into the left atrium 22.

As has been seen, catheter placement is dictated by the type of pressure data desired. It should also be apparent that since health care providers must place catheters in various locations within the cardiovascular system, catheter placement and location is highly important.

Additionally, the anatomy of each individual varies. Likewise, since both hydrostatic pressure and negative pressure heads spoil the accuracy of resulting data, health care providers are desirous of a method and apparatus capable of quickly indicating the location of a catheter that minimizes patient exposure to radiation.

The present invention teaches a novel method and apparatus of achieving this end. Once the indicator 10 and catheter 50 are in position, a chest X-ray may be taken. On examination of the X-ray film the location of the catheter 50 may be seen in relation to the radio opaque fasteners 18.

A level 62 carried by a flexible line 64 with end clips 66, of the type disclosed by Haught, U.S. Pat. No. 4,546,774, may be utilized to bring the hemodynamic transducer assembly 52 into the same horizontal plane as the catheter 50. The transducer assembly 52 may be slidably mounted to an IV stand 46 by an adjustable friction bracket 54.

The zero level 84 of the transducer assembly 52 may be provided with a clip attachment loop 32. A nurse or the like may be provided with a level assembly 6 (62, 64, and 66, FIG. 3). One of the end clips 66 may be connected to the zero level 64 attachment loop 82 of the transducer assembly 52. The other end clip 66 may then be connected to the radio Opaque fastener 18 closest to the catheter level as determined from the X-ray.

In this fashion a patient 74 may be maintained, or repeatedly moved, as comfort or function requires, in any position necessary since the catheter 50 and transducer assembly 52 may be quickly brought into level.

FIG. 1 illustrates the bandage and dressing 48 at the catheter insertion point. Also shown are the pressure infusor 58, microdrip filter 60, and the monitor recorder 56 of a hemodynamic monitoring system.

Whereas, the invention has been disclosed in connection with a preferred embodiment thereof, it is apparent that many modifications, substitutions, and additions may be made thereto which are within the intended broad scope of the appended claims.

Thus, there has been shown and described a catheter position indicator for use in hemodynamic monitoring which accomplishes at least all of the stated objects.

I claim:

1. A catheter position indicator, comprising:
   a radio transparent sheet material containing a plurality of spaced apart radio opaque material potions;
   means for fastening said sheet material to a human body whereby the location of a catheter may be determined in relation to aid radio opaque portions of said radio transparent sheet material with X-rays; and
   flexible line fastening means attached to said radio transparent sheet material in positional relation so said radio opaque material portions whereby a flexible line stretched horizontally from said fastening means will be at a height corresponding to the body portion underlying said sheet material.

2. A method of adjusting a pressure sensitive transducer assembly to the same level as a catheter inserted into a body, said method of leveling comprising the steps of:

locating the relative position of the catheter by placing a radio transparent sheet material containing a plurality of spaced apart radio opaque material portions over the area to be catheterized;

producing an X-ray film of said area to be catheterized;

determining the relative location of said catheter in relation to any of said spaced apart radio opaque portions of said radio transparent sheet material from said X-ray film;

attaching an elongated flexible line carrying a small bubble level intermediate its ends between said transducer assembly and to said radio opaque portion of said transparent sheet material nearest the level of the catheter as shown by said X-ray film; and raising or lowering said transducer assembly to the same level as said catheter as determined by said small bubble level.

3. The catheter position indicator of claim 1, further comprise a plurality of spaced apart fasteners attached to said radio transparent sheet material.

4. The catheter position indicator of claim 1, wherein aid means for fastening said radio transparent sheet material to a human body is a non-toxic tack adhesive.

5. The catheter position indicator of claim 4, further comprising a peel away adhesive protection covering for said non-toxic tack adhesive.

6. A catheter position indicator, comprising:
a radio transparent sheet material containing a plurality of spaced apart radio opaque material portions;
means or fastening said sheet material to a human body, whereby the location for catheter may be determined in relation to said radio opaque portion of said radio transparent sheet material with X-rays; and wherein said plurality of radi opaque portions are formed into a plurality of spaced apart fasteners.

7. A catheter position indicator, comprising:
a radio transparent sheet material containing a plurality of spaced apart radio opaque material portions;
means for fastening said sheet material to a human body, whereby the location of a catheter may be determined in relation to said radio opaque portions of said aradio transparent sheet material with X-rays; and
at least one level engagement means.

8. The catheter position indicator of claim 7, further comprising removable securement means for securing said level engagement means to said transparent sheet material.

9. The catheter position indicator of claim 8, wherein said removable securement means is at least one hook and loop type fastener.

10. The catheter position indicator of claim 8, wherein said removable securement means is an adhesive.

11. A method of determining the relative location of a radio opaque catheter inserted into an area to e catheterized, said locating method comprising the steps of:

placing a radio transparent sheet material containing a plurality of spaced apart radio opaque material fastener portions over the area to be catheterized;

producing an X-ray film of said area to be catheterized; and determining he relative location of said catheter in relation to any of said spaced apart radio opaque fastener portions of said radio transparent sheet material from said X-ray film.

* * * * *